(12) United States Patent
Nandy et al.

(10) Patent No.: US 9,789,178 B2
(45) Date of Patent: *Oct. 17, 2017

(54) DNA SEQUENCE, AND RECOMBINANT PREPARATION OF THE GRASS POLLEN ALLERGEN LOL P 4

(71) Applicant: Merck Patent GmbH, Darmstadt (DE)

(72) Inventors: Andreas Nandy, Hamburg (DE); Helmut Fiebig, Schwarzenbek (DE); Oliver Cromwell, Suesel-Fassendorf (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/535,477

(22) Filed: Nov. 7, 2014

(65) Prior Publication Data

US 2015/0056229 A1 Feb. 26, 2015

Related U.S. Application Data

(60) Continuation of application No. 12/961,034, filed on Dec. 6, 2010, now Pat. No. 8,945,530, which is a division of application No. 10/583,093, filed as application No. PCT/EP2004/013663 on Dec. 1, 2004, now Pat. No. 7,846,448.

(30) Foreign Application Priority Data

Dec. 16, 2003 (DE) .................................... 10359352

(51) Int. Cl.
| | |
|---|---|
| *A61K 39/35* | (2006.01) |
| *C07K 14/415* | (2006.01) |
| *A61K 39/00* | (2006.01) |

(52) U.S. Cl.
CPC ............ *A61K 39/35* (2013.01); *C07K 14/415* (2013.01); *A61K 39/00* (2013.01)

(58) Field of Classification Search
None
See application file for complete search history.

(56) References Cited

U.S. PATENT DOCUMENTS

| | | | |
|---|---|---|---|
| 6,759,234 B1 | 7/2004 | Gefter et al. | |
| 7,846,448 B2* | 12/2010 | Nandy ................... | A61K 39/35 424/185.1 |
| 8,945,530 B2* | 2/2015 | Nandy ................. | C07K 14/415 424/93.2 |
| 2007/0020621 A1 | 1/2007 | Boukharov et al. | |
| 2007/0154496 A1 | 7/2007 | Nandy et al. | |

FOREIGN PATENT DOCUMENTS

| | | |
|---|---|---|
| WO | 9607428 | 3/1996 |
| WO | 2004000881 | 12/2003 |

OTHER PUBLICATIONS

Zolkipli et al. 'Randomized controlled trial of primary prevention of atopy using house dust mite allergen oral immunotherapy in early childhood.' J. Allerg. Clin. Immunol. 136(6):1541-1547, 20015.*
Hartl et al., "DNA vaccines for allergy treatment", Methods 32:328-339, 2004.
Kuby et al., "Immunology", Fourth Edition, Chapter 18: 449-465, Jan. 15, 2000.
Brenner S., "Errors in genome annotation", Trends in Genetics 15:132-133, 1999.
Bowie et al., "Decipering the Message in Protein Sequences: Tolerance to Amino Acid Substitutions", Science 247:1306-1310, 1990.
Meinkoth et al., "Hybridization of nucleic acids immobilized on solid supports", Anal. Biochem. 138:267-284, 1984.
Ali et al., "Normalisation of Cereal Endosperm EST Libraries for Structural and Functional Genomic Analysis", Plant Molecular Biology Reporter 18: 123-132, 2000.
Metzler et al., "Solution structure of-uman CTLA-4 and delineation of a CD80/CD86 binding site conserved in CD28", Nature Structural Biol. 4:527-531, 1997.
Bork et al., "Powers and Pitfalls in Sequence Analysis: The 70% Hurdle", Gen. Res. 10:398-400, 2000.
Doerks et al., "Protein annotation: detective work for function prediction", Trends in Genetics, 14:248-250, 1998.
Smith et al., "The challenges of genome sequence annotation or "The devil is in the details"", Nat. Biotech. 15:1222-1223, 1997.
Prescott et al., "Novel Immunomodulatory Strategies for the Prevention of Atopy and Asthma", Allergy Frontiers: Therapy and Prevention 5( I):417-432, 2010.
http://www.allergen.org/viewallergen.php?aid=419[Jul. 28, 2011 7:26:57 PM].
Ekramoddoullah A K M, et al: "Immunochemical Characterization of a High Molecular Weight Basic Allergen of Rye Grass Lolium-Perenne Pollen" Molecular Immunology, Bd. 20, Nr. 4, 1983, pp. 465-474, XP002323104; ISSN: 0161-5890.
Jaggi K et al: "Identificationof Two Distinct Allergenic Sites on Ryegrass Pollen Allergen LOL P IV" Journal of Allergy and Clinical Immunology, Bd. 83, Nr. 4, 1989, pp. 845-852, XP009045856, ISSN: 0091-6749.
Jaggi et al: "Allergenic Fragments of Ryegrass Lolium-Perenne Pollen Allergen LOL P-IV" International Archives of Allergy and Applied Immunology, Bd. 89, Nr. 4, 1989, pp. 342-348; XP009045855; ISSN: 0020-5915.

(Continued)

*Primary Examiner* — Nora Rooney
(74) *Attorney, Agent, or Firm* — Millen, White, Zelano, Branigan, P.C.

(57) ABSTRACT

The present invention relates to the provision of a DNA sequence of the major grass pollen allergen Lol p 4. The invention also encompasses fragments, new combinations of partial sequences and point mutants having a hypoallergenic action. The recombinant DNA molecules and the derived polypeptides, fragments, new combinations of partial sequences and variants can be utilized for the therapy of pollen-allergic diseases. The proteins prepared by recombinant methods can be employed for in vitro and in vivo diagnosis of pollen allergies.

8 Claims, No Drawings

(56) References Cited

OTHER PUBLICATIONS

Fahlbusch et al. "Detection and Quantification of Group 4 Allergens in Grass Pollen Extracts Using Monoclonal Antibodies" Clinical and Experimental Allergy, Blackwell Scientific Publications, London, GB, Bd. 28, Nr. 7, Jul. 1998, pp. 799-807, XP002260345.
Databas EMBL; Nov. 19, 2004; "Lolium Perenne Partial LOLP4 Gene for Pollen Allergen LOL P4." XP002323105.
Focke et al., "Nonanaphylactic Synthetic Peptides Derived From B Cell Epitopes of the Major Grass Pollen Allergen", PHL. P. 1, for Allergy Vaccination. FASEB Journal, vol. 15:, 2001, pp. 2042-2044.
Tarzi et al., "Pepetide Immunotherapy for Allergic Disease", Expert. Opin. Biol. Ther. vol. 3 (4): 2003, pp. 617-626.
Zhou et al., "Regulation of Levels of Serum Antibodies to Ryegrass Pollen Allergen LOL. PIV by an Internal Image Anti-Idiotypic Monoclonal Antibody." Immunolgy, vol. 84: 1995, pp. 343-349.
Bose et al., "Human and Murine Antibodies to Rye Grass Pollen Allergen LOLPIV Share a Common Idiotope", Immunology, vol. 63, 1998, pp. 579-584.

\* cited by examiner

SEQUENCE LISTING

```
<160> NUMBER OF SEQ ID NOS: 27

<210> SEQ ID NO 1
<211> LENGTH: 1272
<212> TYPE: DNA
<213> ORGANISM: Lolium perenne
<220> FEATURE:
<221> NAME/KEY: CDS
<222> LOCATION: (2)..(1270)

<400> SEQUENCE: 1 t gcc gtg gtg tgc ggc cgc cgt tac gac gtc cgc atc cgc gta cgc agc        49
  Ala Val Val Cys Gly Arg Arg Tyr Asp Val Arg Ile Arg Val Arg Ser
   1               5                  10                  15 ggc ggg cac gac tac gag ggc ctc tcg tac cgc tcc ctg cag ccc gag          97
Gly Gly His Asp Tyr Glu Gly Leu Ser Tyr Arg Ser Leu Gln Pro Glu
             20                  25                  30 aac ttc gca gtc gtc gac ctc aac cag atg cgg gcg gtg ttg gtg gac         145
Asn Phe Ala Val Val Asp Leu Asn Gln Met Arg Ala Val Leu Val Asp
         35                  40                  45 ggt aag gcc cgc acg gcg tgg gtc gac tcc ggc gcg cag ctc ggc gag         193
Gly Lys Ala Arg Thr Ala Trp Val Asp Ser Gly Ala Gln Leu Gly Glu
     50                  55                  60 ctc tac tac gcc atc tcc aag tat agc cgc acg ctg gcc ttc ccg gca         241
Leu Tyr Tyr Ala Ile Ser Lys Tyr Ser Arg Thr Leu Ala Phe Pro Ala
 65                  70                  75                  80 ggc gtt tgc ccg acc atc ggc gtg ggc ggc aac ctc gcg ggc ggc ggc         289
Gly Val Cys Pro Thr Ile Gly Val Gly Gly Asn Leu Ala Gly Gly Gly
                 85                  90                  95 ttc ggt atg ctg ctg cgc aag tac ggc atc gcc gca gag aac gtc atc         337
Phe Gly Met Leu Leu Arg Lys Tyr Gly Ile Ala Ala Glu Asn Val Ile
            100                 105                 110 gac gtg aag ctc gtc gac gcc aac ggc aag ctc cac gac aag aag tcc         385
Asp Val Lys Leu Val Asp Ala Asn Gly Lys Leu His Asp Lys Lys Ser
        115                 120                 125 atg ggc gac gac cat ttc tgg gcc gtg agg ggt ggc ggc ggc gag agc         433
```

```
                Met Gly Asp Asp His Phe Trp Ala Val Arg Gly Gly Gly Glu Ser
                    130                 135                 140 ttc ggc atc gtg gtc tcg tgg cag gtg aag ctc ctg ccg gtg cct ccc        481
Phe Gly Ile Val Val Ser Trp Gln Val Lys Leu Leu Pro Val Pro Pro
145                 150                 155                 160 acg gtg acc atc ttc aag atc ccc aag tca gtc agc gag ggc gcc gtg        529
Thr Val Thr Ile Phe Lys Ile Pro Lys Ser Val Ser Glu Gly Ala Val
                165                 170                 175 gac atc atc aac aag tgg caa ctg gtc gcg cct caa ctt ccc gcc gac        577
Asp Ile Ile Asn Lys Trp Gln Leu Val Ala Pro Gln Leu Pro Ala Asp
            180                 185                 190 ctc atg atc cgc atc att gcg atg ggg ccc aag gcc acg ttc gag gcc        625
Leu Met Ile Arg Ile Ile Ala Met Gly Pro Lys Ala Thr Phe Glu Ala
        195                 200                 205 atg tac ctc ggc acc tgc aaa acc ctg acg ccg atg atg cag agc aag        673
Met Tyr Leu Gly Thr Cys Lys Thr Leu Thr Pro Met Met Gln Ser Lys
    210                 215                 220 ttc ccc gag ctt ggc atg aac gcc tcg cac tgc aac gag atg tca tgg        721
Phe Pro Glu Leu Gly Met Asn Ala Ser His Cys Asn Glu Met Ser Trp
225                 230                 235                 240 atc gag tcc atc ccc ttc gtc cac ctc ggc cat agg gat tcc ctg gag        769
Ile Glu Ser Ile Pro Phe Val His Leu Gly His Arg Asp Ser Leu Glu
                245                 250                 255 ggc gac ctc ctc aac cgg aac aac acc ttc aag ccc ttt gcg gag tac        817
Gly Asp Leu Leu Asn Arg Asn Asn Thr Phe Lys Pro Phe Ala Glu Tyr
                260                 265                 270 aaa tcg gac tac gtc tac gag cca ttc ccc aag agc gtg tgg gag cag        865
Lys Ser Asp Tyr Val Tyr Glu Pro Phe Pro Lys Ser Val Trp Glu Gln
            275                 280                 285 atc ttc ggc acc tgg ctc gtg aag cct ggt gcg ggg att atg atc ttt        913
Ile Phe Gly Thr Trp Leu Val Lys Pro Gly Ala Gly Ile Met Ile Phe
        290                 295                 300 gac ccc tac ggt gcc acc atc agc gct acc cca gaa gcg gcg acg ccg        961
Asp Pro Tyr Gly Ala Thr Ile Ser Ala Thr Pro Glu Ala Ala Thr Pro
305                 310                 315                 320 ttc cct cac cgc aag gga gtc ctc ttc aac atc cag tac gtc aac tac       1009
Phe Pro His Arg Lys Gly Val Leu Phe Asn Ile Gln Tyr Val Asn Tyr
                325                 330                 335 tgg ttc gct ccg gga gcc ggc gcc gcg ccc ttg tca tgg agc aag gaa       1057
Trp Phe Ala Pro Gly Ala Gly Ala Ala Pro Leu Ser Trp Ser Lys Glu
                340                 345                 350 atc tac aac tac atg gag ccg tac gtg agc aag aac ccc agg cag gcc       1105
Ile Tyr Asn Tyr Met Glu Pro Tyr Val Ser Lys Asn Pro Arg Gln Ala
            355                 360                 365 tac gcc aac tac agg gac atc gac ctc ggg agg aac gag gtg gtg aat       1153
Tyr Ala Asn Tyr Arg Asp Ile Asp Leu Gly Arg Asn Glu Val Val Asn
        370                 375                 380 ggc gtc tcc acc tac agc agt ggt aag gtc tgg gga cag aaa tat ttc       1201
Gly Val Ser Thr Tyr Ser Ser Gly Lys Val Trp Gly Gln Lys Tyr Phe
385                 390                 395                 400 aag ggt aac ttc gag agg ctc gcc att acc aag ggc aag gtg gat cct       1249
Lys Gly Asn Phe Glu Arg Leu Ala Ile Thr Lys Gly Lys Val Asp Pro
                405                 410                 415 acg gat tac ttc agg aac gag ca                                         1272
Thr Asp Tyr Phe Arg Asn Glu
            420

<210> SEQ ID NO 2
<211> LENGTH: 423
<212> TYPE: PRT
```

<213> ORGANISM: Lolium perenne

<400> SEQUENCE: 2

```
Ala Val Val Cys Gly Arg Arg Tyr Asp Val Arg Ile Arg Val Arg Ser
 1               5                  10                  15

Gly Gly His Asp Tyr Glu Gly Leu Ser Tyr Arg Ser Leu Gln Pro Glu
            20                  25                  30

Asn Phe Ala Val Val Asp Leu Asn Gln Met Arg Ala Val Leu Val Asp
        35                  40                  45

Gly Lys Ala Arg Thr Ala Trp Val Asp Ser Gly Ala Gln Leu Gly Glu
    50                  55                  60

Leu Tyr Tyr Ala Ile Ser Lys Tyr Ser Arg Thr Leu Ala Phe Pro Ala
65                  70                  75                  80

Gly Val Cys Pro Thr Ile Gly Val Gly Gly Asn Leu Ala Gly Gly Gly
                85                  90                  95

Phe Gly Met Leu Leu Arg Lys Tyr Gly Ile Ala Ala Glu Asn Val Ile
            100                 105                 110

Asp Val Lys Leu Val Asp Ala Asn Gly Lys Leu His Asp Lys Lys Ser
        115                 120                 125

Met Gly Asp Asp His Phe Trp Ala Val Arg Gly Gly Gly Gly Glu Ser
    130                 135                 140

Phe Gly Ile Val Val Ser Trp Gln Val Lys Leu Leu Pro Val Pro Pro
145                 150                 155                 160

Thr Val Thr Ile Phe Lys Ile Pro Lys Ser Val Ser Glu Gly Ala Val
                165                 170                 175

Asp Ile Ile Asn Lys Trp Gln Leu Val Ala Pro Gln Leu Pro Ala Asp
            180                 185                 190

Leu Met Ile Arg Ile Ile Ala Met Gly Pro Lys Ala Thr Phe Glu Ala
        195                 200                 205

Met Tyr Leu Gly Thr Cys Lys Thr Leu Thr Pro Met Met Gln Ser Lys
    210                 215                 220

Phe Pro Glu Leu Gly Met Asn Ala Ser His Cys Asn Glu Met Ser Trp
225                 230                 235                 240

Ile Glu Ser Ile Pro Phe Val His Leu Gly His Arg Asp Ser Leu Glu
                245                 250                 255

Gly Asp Leu Leu Asn Arg Asn Asn Thr Phe Lys Pro Phe Ala Glu Tyr
            260                 265                 270

Lys Ser Asp Tyr Val Tyr Glu Pro Phe Pro Lys Ser Val Trp Glu Gln
        275                 280                 285

Ile Phe Gly Thr Trp Leu Val Lys Pro Gly Ala Gly Ile Met Ile Phe
    290                 295                 300

Asp Pro Tyr Gly Ala Thr Ile Ser Ala Thr Pro Glu Ala Ala Thr Pro
305                 310                 315                 320

Phe Pro His Arg Lys Gly Val Leu Phe Asn Ile Gln Tyr Val Asn Tyr
                325                 330                 335

Trp Phe Ala Pro Gly Ala Gly Ala Pro Leu Ser Trp Ser Lys Glu
            340                 345                 350

Ile Tyr Asn Tyr Met Glu Pro Tyr Val Ser Lys Asn Pro Arg Gln Ala
        355                 360                 365

Tyr Ala Asn Tyr Arg Asp Ile Asp Leu Gly Arg Asn Glu Val Val Asn
    370                 375                 380

Gly Val Ser Thr Tyr Ser Ser Gly Lys Val Trp Gly Gln Lys Tyr Phe
385                 390                 395                 400
```

-continued

```
Lys Gly Asn Phe Glu Arg Leu Ala Ile Thr Lys Gly Lys Val Asp Pro
                405                 410                 415
Thr Asp Tyr Phe Arg Asn Glu
            420

<210> SEQ ID NO 3
<211> LENGTH: 1503
<212> TYPE: DNA
<213> ORGANISM: Lolium perenne
<220> FEATURE:
<221> NAME/KEY: CDS
<222> LOCATION: (1)..(1503)

<400> SEQUENCE: 3 tac ttc ccg ccg ccg gct gct aaa gaa gac ttc ctg ggt tgc ctg gtt      48
Tyr Phe Pro Pro Pro Ala Ala Lys Glu Asp Phe Leu Gly Cys Leu Val
 1               5                  10                  15 aaa gaa atc ccg ccg cgt ctg ttg tac gcg aaa tcg tcg ccg gcg tat      96
Lys Glu Ile Pro Pro Arg Leu Leu Tyr Ala Lys Ser Ser Pro Ala Tyr
                20                  25                  30 ccc tca gtc ctg ggg cag acc atc cgg aac tcg agg tgg tcg tcg ccg     144
Pro Ser Val Leu Gly Gln Thr Ile Arg Asn Ser Arg Trp Ser Ser Pro
            35                  40                  45 gac aac gtg aag ccg ctc tac atc atc acc ccc acc aac gtc tcc cac     192
Asp Asn Val Lys Pro Leu Tyr Ile Ile Thr Pro Thr Asn Val Ser His
        50                  55                  60 atc cag tct gcc gtg gtg tgc ggc cgc cgt tac gac gtc cgc atc cgc     240
Ile Gln Ser Ala Val Val Cys Gly Arg Arg Tyr Asp Val Arg Ile Arg
65                  70                  75                  80 gta cgc agc ggc ggg cac gac tac gag ggc ctc tcg tac cgc tcc ctg     288
Val Arg Ser Gly Gly His Asp Tyr Glu Gly Leu Ser Tyr Arg Ser Leu
                85                  90                  95 cag ccc gag aac ttc gca gtc gtc gac ctc aac cag atg cgg gcg gtg     336
Gln Pro Glu Asn Phe Ala Val Val Asp Leu Asn Gln Met Arg Ala Val
                100                 105                 110 ttg gtg gac ggt aag gcc cgc acg gcg tgg gtc gac tcc ggc gcg cag     384
Leu Val Asp Gly Lys Ala Arg Thr Ala Trp Val Asp Ser Gly Ala Gln
            115                 120                 125 ctc ggc gag ctc tac tac gcc atc tcc aag tat agc cgc acg ctg gcc     432
Leu Gly Glu Leu Tyr Tyr Ala Ile Ser Lys Tyr Ser Arg Thr Leu Ala
        130                 135                 140 ttc ccg gca ggc gtt tgc ccg acc atc ggc gtg ggc ggc aac ctc gcg     480
Phe Pro Ala Gly Val Cys Pro Thr Ile Gly Val Gly Gly Asn Leu Ala
145                 150                 155                 160 ggc ggc ggc ttc ggt atg ctg ctg cgc aag tac ggc atc gcc gca gag     528
Gly Gly Gly Phe Gly Met Leu Leu Arg Lys Tyr Gly Ile Ala Ala Glu
                165                 170                 175 aac gtc atc gac gtg aag ctc gtc gac gcc aac ggc aag ctg cac gac     576
Asn Val Ile Asp Val Lys Leu Val Asp Ala Asn Gly Lys Leu His Asp
                180                 185                 190 aag aag tcc atg ggc gac gac cat ttc tgg gcc gtg agg ggt ggc ggc     624
Lys Lys Ser Met Gly Asp Asp His Phe Trp Ala Val Arg Gly Gly Gly
            195                 200                 205 ggc gag agc ttc ggc atc gtg gtc tcg tgg cag gtg aag ctc ctg ccg     672
Gly Glu Ser Phe Gly Ile Val Val Ser Trp Gln Val Lys Leu Leu Pro
        210                 215                 220 gtg cct ccc acg gtg acc atc ttc aag atc ccc aag tca gtc agc gag     720
Val Pro Pro Thr Val Thr Ile Phe Lys Ile Pro Lys Ser Val Ser Glu
225                 230                 235                 240 ggc gcc gtg gac atc atc aac aag tgg caa ctg gtc gcg cct caa ctt     768
Gly Ala Val Asp Ile Ile Asn Lys Trp Gln Leu Val Ala Pro Gln Leu
```

-continued

| | | |
|---|---|---|
| ccc gcc gac ctc atg atc cgc atc att gcg atg ggg ccc aag gcc acg<br>Pro Ala Asp Leu Met Ile Arg Ile Ile Ala Met Gly Pro Lys Ala Thr<br>260                       265                      270 | 816 |
| ttc gag gcc atg tac ctc ggc acc tgc aaa acc ctg acg ccg atg atg<br>Phe Glu Ala Met Tyr Leu Gly Thr Cys Lys Thr Leu Thr Pro Met Met<br>275                       280                      285 | 864 |
| cag agc aag ttc ccc gag ctt ggc atg aac gcc tcg cac tgc aac gag<br>Gln Ser Lys Phe Pro Glu Leu Gly Met Asn Ala Ser His Cys Asn Glu<br>290                       295                      300 | 912 |
| atg tca tgg atc gag tcc atc ccc ttc gtc cac ctc ggc cat agg gat<br>Met Ser Trp Ile Glu Ser Ile Pro Phe Val His Leu Gly His Arg Asp<br>305                       310                      315                      320 | 960 |
| tcc ctg gag ggc gac ctc ctc aac cgg aac aac acc ttc aag ccc ttt<br>Ser Leu Glu Gly Asp Leu Leu Asn Arg Asn Asn Thr Phe Lys Pro Phe<br>325                       330                      335 | 1008 |
| gcg gag tac aaa tcg gac tac gtc tac gag cca ttc ccc aag agc gtg<br>Ala Glu Tyr Lys Ser Asp Tyr Val Tyr Glu Pro Phe Pro Lys Ser Val<br>340                       345                      350 | 1056 |
| tgg gag cag atc ttc ggc acc tgg ctc gtg aag cct ggt gcg ggg att<br>Trp Glu Gln Ile Phe Gly Thr Trp Leu Val Lys Pro Gly Ala Gly Ile<br>355                       360                      365 | 1104 |
| atg atc ttt gac ccc tac ggt gcc acc atc agc gct acc cca gaa gcg<br>Met Ile Phe Asp Pro Tyr Gly Ala Thr Ile Ser Ala Thr Pro Glu Ala<br>370                       375                      380 | 1152 |
| gcg acg ccg ttc cct cac cgc aag gga gtc ctc ttc aac atc cag tac<br>Ala Thr Pro Phe Pro His Arg Lys Gly Val Leu Phe Asn Ile Gln Tyr<br>385                       390                      395                      400 | 1200 |
| gtc aac tac tgg ttc gct ccg gga gcc ggc gcc gcc ccc ttg tca tgg<br>Val Asn Tyr Trp Phe Ala Pro Gly Ala Gly Ala Ala Pro Leu Ser Trp<br>405                       410                      415 | 1248 |
| agc aag gaa atc tac aac tac atg gag ccg tac gtg agc aag aac ccc<br>Ser Lys Glu Ile Tyr Asn Tyr Met Glu Pro Tyr Val Ser Lys Asn Pro<br>420                       425                      430 | 1296 |
| agg cag gcc tac gcc aac tac agg gac atc gac ctc ggg agg aac gag<br>Arg Gln Ala Tyr Ala Asn Tyr Arg Asp Ile Asp Leu Gly Arg Asn Glu<br>435                       440                      445 | 1344 |
| gtg gtg aat ggc gtc tcc acc tac agc agt ggt aag gtc tgg gga cag<br>Val Val Asn Gly Val Ser Thr Tyr Ser Ser Gly Lys Val Trp Gly Gln<br>450                       455                      460 | 1392 |
| aaa tat ttc aag ggt aac ttc gag agg ctc gcc att acc aag ggc aag<br>Lys Tyr Phe Lys Gly Asn Phe Glu Arg Leu Ala Ile Thr Lys Gly Lys<br>465                       470                      475                      480 | 1440 |
| gtg gat cct acg gat tac ttc agg aac gag cag agc atc ccg ccg ctc<br>Val Asp Pro Thr Asp Tyr Phe Arg Asn Glu Gln Ser Ile Pro Pro Leu<br>485                       490                      495 | 1488 |
| atc aaa aag tac tga<br>Ile Lys Lys Tyr<br>500 | 1503 |

<210> SEQ ID NO 4
<211> LENGTH: 500
<212> TYPE: PRT
<213> ORGANISM: Lolium perenne

<400> SEQUENCE: 4

Tyr Phe Pro Pro Pro Ala Ala Lys Glu Asp Phe Leu Gly Cys Leu Val
1                 5                    10                  15

Lys Glu Ile Pro Pro Arg Leu Leu Tyr Ala Lys Ser Ser Pro Ala Tyr
                20                    25                    30

```
Pro Ser Val Leu Gly Gln Thr Ile Arg Asn Ser Arg Trp Ser Ser Pro
        35                  40                  45

Asp Asn Val Lys Pro Leu Tyr Ile Ile Thr Pro Thr Asn Val Ser His
    50                  55                  60

Ile Gln Ser Ala Val Val Cys Gly Arg Tyr Asp Val Arg Ile Arg
65                  70                  75                  80

Val Arg Ser Gly Gly His Asp Tyr Glu Gly Leu Ser Tyr Arg Ser Leu
                    85                  90                  95

Gln Pro Glu Asn Phe Ala Val Val Asp Leu Asn Gln Met Arg Ala Val
                100                 105                 110

Leu Val Asp Gly Lys Ala Arg Thr Ala Trp Val Asp Ser Gly Ala Gln
                115                 120                 125

Leu Gly Glu Leu Tyr Tyr Ala Ile Ser Lys Tyr Ser Arg Thr Leu Ala
            130                 135                 140

Phe Pro Ala Gly Val Cys Pro Thr Ile Gly Val Gly Gly Asn Leu Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Lys Leu His Asp
                180                 185                 190

Lys Lys Ser Met Gly Asp Asp His Phe Trp Ala Val Arg Gly Gly Gly
            195                 200                 205

Gly Glu Ser Phe Gly Ile Val Val Ser Trp Gln Val Lys Leu Leu Pro
            210                 215                 220

Val Pro Pro Thr Val Thr Ile Phe Lys Ile Pro Lys Ser Val Ser Glu
225                 230                 235                 240

Gly Ala Val Asp Ile Ile Asn Lys Trp Gln Leu Val Ala Pro Gln Leu
                245                 250                 255

Pro Ala Asp Leu Met Ile Arg Ile Ile Ala Met Gly Pro Lys Ala Thr
                260                 265                 270

Phe Glu Ala Met Tyr Leu Gly Thr Cys Lys Thr Leu Thr Pro Met Met
            275                 280                 285

Gln Ser Lys Phe Pro Glu Leu Gly Met Asn Ala Ser His Cys Asn Glu
        290                 295                 300

Met Ser Trp Ile Glu Ser Ile Pro Phe Val His Leu Gly His Arg Asp
305                 310                 315                 320

Ser Leu Glu Gly Asp Leu Leu Asn Arg Asn Asn Thr Phe Lys Pro Phe
                325                 330                 335

Ala Glu Tyr Lys Ser Asp Tyr Val Tyr Glu Pro Phe Pro Lys Ser Val
            340                 345                 350

Trp Glu Gln Ile Phe Gly Thr Trp Leu Val Lys Pro Gly Ala Gly Ile
            355                 360                 365

Met Ile Phe Asp Pro Tyr Gly Ala Thr Ile Ser Ala Thr Pro Glu Ala
        370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Gly Ala Ala Pro Leu Ser Trp
                405                 410                 415

Ser Lys Glu Ile Tyr Asn Tyr Met Glu Pro Tyr Val Ser Lys Asn Pro
            420                 425                 430

Arg Gln Ala Tyr Ala Asn Tyr Arg Asp Ile Asp Leu Gly Arg Asn Glu
        435                 440                 445
```

```
                     Val Val Asn Gly Val Ser Thr Tyr Ser Ser Gly Lys Val Trp Gly Gln
                         450                 455                 460

Lys Tyr Phe Lys Gly Asn Phe Glu Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
            500

<210> SEQ ID NO 5
<211> LENGTH: 1503
<212> TYPE: DNA
<213> ORGANISM: Phleum pratense
<220> FEATURE:
<221> NAME/KEY: CDS
<222> LOCATION: (1)..(1503)

<400> SEQUENCE: 5 tac ttc ccg ccg ccg gct gct aaa gaa gac ttc ctg ggt tgc ctg gtt     48
Tyr Phe Pro Pro Pro Ala Ala Lys Glu Asp Phe Leu Gly Cys Leu Val
  1               5                  10                  15 aaa gaa atc ccg ccg cgt ctg ttg tac gcg aaa tcg tcg ccg gcg tat     96
Lys Glu Ile Pro Pro Arg Leu Leu Tyr Ala Lys Ser Ser Pro Ala Tyr
                 20                  25                  30 ccc tca gtc ctg ggg cag acc atc cgg aac tcg agg tgg tcg tcg ccg    144
Pro Ser Val Leu Gly Gln Thr Ile Arg Asn Ser Arg Trp Ser Ser Pro
             35                  40                  45 gac aac gtg aag ccg ctc tac atc atc acc ccc acc aac gtc tcc cac    192
Asp Asn Val Lys Pro Leu Tyr Ile Ile Thr Pro Thr Asn Val Ser His
         50                  55                  60 atc cag tcc gcc gtg gtg tgc ggc cgc cgc cac agc gtc cgc atc cgc    240
Ile Gln Ser Ala Val Val Cys Gly Arg Arg His Ser Val Arg Ile Arg
 65                  70                  75                  80 gtg cgc agc ggc ggg cac gac tac gag ggc ctc tcg tac cgg tct ttg    288
Val Arg Ser Gly Gly His Asp Tyr Glu Gly Leu Ser Tyr Arg Ser Leu
                 85                  90                  95 cag ccc gag acg ttc gcc gtc gtc gac ctc aac aag atg cgg gcg gtg    336
Gln Pro Glu Thr Phe Ala Val Val Asp Leu Asn Lys Met Arg Ala Val
            100                 105                 110 tgg gtg gac ggc aag gcc cgc acg gcg tgg gtg gac tcc ggc gcg cag    384
Trp Val Asp Gly Lys Ala Arg Thr Ala Trp Val Asp Ser Gly Ala Gln
        115                 120                 125 ctc ggc gag ctc tac tac gcc atc tat aag gcg agc ccc acg ctg gcg    432
Leu Gly Glu Leu Tyr Tyr Ala Ile Tyr Lys Ala Ser Pro Thr Leu Ala
    130                 135                 140 ttc ccg gcc ggc gtg tgc ccg acg atc gga gtg ggc ggc aac ttc gcg    480
Phe Pro Ala Gly Val Cys Pro Thr Ile Gly Val Gly Gly Asn Phe Ala
145                 150                 155                 160 ggc ggc ggc ttc ggc atg ctg ctg cgc aag tac ggc atc gcc gcg gag    528
Gly Gly Gly Phe Gly Met Leu Leu Arg Lys Tyr Gly Ile Ala Ala Glu
                165                 170                 175 aac gtc atc gac gtg aag ctc gtc gac gcc aac ggc aag ctg cac gac    576
Asn Val Ile Asp Val Lys Leu Val Asp Ala Asn Gly Lys Leu His Asp
            180                 185                 190 aag aag tcc atg ggc gac gac cat ttc tgg gcc gtc agg ggc ggc ggg    624
Lys Lys Ser Met Gly Asp Asp His Phe Trp Ala Val Arg Gly Gly Gly
        195                 200                 205 ggc gag agc ttc ggc atc gtg gtc gcg tgg cag gtg aag ctc ctg ccg    672
Gly Glu Ser Phe Gly Ile Val Val Ala Trp Gln Val Lys Leu Leu Pro
    210                 215                 220
```

```
gtg ccg ccc acc gtg aca ata ttc aag atc tcc aag aca gtg agc gag      720
Val Pro Pro Thr Val Thr Ile Phe Lys Ile Ser Lys Thr Val Ser Glu
225             230                 235                 240 ggc gcc gtg gac atc atc aac aag tgg caa gtg gtc gcg ccg cag ctt      768
Gly Ala Val Asp Ile Ile Asn Lys Trp Gln Val Val Ala Pro Gln Leu
                245                 250                 255 ccc gcc gac ctc atg atc cgc atc atc gcg cag ggg ccc aag gcc acg      816
Pro Ala Asp Leu Met Ile Arg Ile Ile Ala Gln Gly Pro Lys Ala Thr
            260                 265                 270 ttc gag gcc atg tac ctc ggc acc tgc aaa acc ctg acg ccg ttg atg      864
Phe Glu Ala Met Tyr Leu Gly Thr Cys Lys Thr Leu Thr Pro Leu Met
        275                 280                 285 agc agc aag ttc ccg gag ctc ggc atg aac ccc tcc cac tgc aac gag      912
Ser Ser Lys Phe Pro Glu Leu Gly Met Asn Pro Ser His Cys Asn Glu
    290                 295                 300 atg tca tgg atc cag tcc atc ccc ttc gtc cac ctc ggc cac agg gac      960
Met Ser Trp Ile Gln Ser Ile Pro Phe Val His Leu Gly His Arg Asp
305                 310                 315                 320 gcc ctc gag gac gac ctc ctc aac cgg aac aac tcc ttc aag ccc ttc     1008
Ala Leu Glu Asp Asp Leu Leu Asn Arg Asn Asn Ser Phe Lys Pro Phe
                325                 330                 335 gcc gaa tac aag tcc gac tac gtc tac cag ccc ttc ccc aag acc gtc     1056
Ala Glu Tyr Lys Ser Asp Tyr Val Tyr Gln Pro Phe Pro Lys Thr Val
            340                 345                 350 tgg gag cag atc ctc aac acc tgg ctc gtc aag ccc ggc gcc ggg atc     1104
Trp Glu Gln Ile Leu Asn Thr Trp Leu Val Lys Pro Gly Ala Gly Ile
        355                 360                 365 atg atc ttc gac ccc tac ggc gcc acc atc agc gcc acc ccg gag tcc     1152
Met Ile Phe Asp Pro Tyr Gly Ala Thr Ile Ser Ala Thr Pro Glu Ser
370                 375                 380 gcc acg ccc ttc cct cac cgc aag ggc gtc ctc ttc aac atc cag tac     1200
Ala Thr Pro Phe Pro His Arg Lys Gly Val Leu Phe Asn Ile Gln Tyr
385                 390                 395                 400 gtc aac tac tgg ttc gcc ccg gga gcc gcc gcc gcg ccc ctc tcg tgg     1248
Val Asn Tyr Trp Phe Ala Pro Gly Ala Ala Ala Ala Pro Leu Ser Trp
                405                 410                 415 agc aag gac atc tac aac tac atg gag ccc tac gtg agc aag aac ccc     1296
Ser Lys Asp Ile Tyr Asn Tyr Met Glu Pro Tyr Val Ser Lys Asn Pro
            420                 425                 430 agg cag gcg tac gca aac tac agg gac atc gac ctc ggc agg aac gag     1344
Arg Gln Ala Tyr Ala Asn Tyr Arg Asp Ile Asp Leu Gly Arg Asn Glu
        435                 440                 445 gtg gtc aac gac gtc tcc acc tac gcc agc ggc aag gtc tgg ggc cag     1392
Val Val Asn Asp Val Ser Thr Tyr Ala Ser Gly Lys Val Trp Gly Gln
450                 455                 460 aaa tac ttc aag ggc aac ttc gag agg ctc gcc att acc aag ggc aag     1440
Lys Tyr Phe Lys Gly Asn Phe Glu Arg Leu Ala Ile Thr Lys Gly Lys
465                 470                 475                 480 gtc gat cct acc gac tac ttc agg aac gag cag agc atc ccg ccg ctc     1488
Val Asp Pro Thr Asp Tyr Phe Arg Asn Glu Gln Ser Ile Pro Pro Leu
                485                 490                 495 atc aaa aag tac tga                                                  1503
Ile Lys Lys Tyr
            500
```

<210> SEQ ID NO 6
<211> LENGTH: 500
<212> TYPE: PRT
<213> ORGANISM: Phleum pratense

<400> SEQUENCE: 6

-continued

```
Tyr Phe Pro Pro Ala Ala Lys Glu Asp Phe Leu Gly Cys Leu Val
  1               5                  10                  15

Lys Glu Ile Pro Pro Arg Leu Leu Tyr Ala Lys Ser Ser Pro Ala Tyr
                 20                  25                  30

Pro Ser Val Leu Gly Gln Thr Ile Arg Asn Ser Arg Trp Ser Ser Pro
         35                  40                  45

Asp Asn Val Lys Pro Leu Tyr Ile Ile Thr Pro Thr Asn Val Ser His
     50                  55                  60

Ile Gln Ser Ala Val Val Cys Gly Arg Arg His Ser Val Arg Ile Arg
 65              70                  75                      80

Val Arg Ser Gly Gly His Asp Tyr Glu Gly Leu Ser Tyr Arg Ser Leu
                 85                  90                  95

Gln Pro Glu Thr Phe Ala Val Val Asp Leu Asn Lys Met Arg Ala Val
                100                 105                 110

Trp Val Asp Gly Lys Ala Arg Thr Ala Trp Val Asp Ser Gly Ala Gln
             115                 120                 125

Leu Gly Glu Leu Tyr Tyr Ala Ile Tyr Lys Ala Ser Pro Thr Leu Ala
         130                 135                 140

Phe Pro Ala Gly Val Cys Pro Thr Ile Gly Val Gly Gly Asn Phe Ala
145                 150                 155                 160

Gly Gly Gly Phe Gly Met Leu Leu Arg Lys Tyr Gly Ile Ala Ala Glu
             165                 170                 175

Asn Val Ile Asp Val Lys Leu Val Asp Ala Asn Gly Lys Leu His Asp
             180                 185                 190

Lys Lys Ser Met Gly Asp Asp His Phe Trp Ala Val Arg Gly Gly Gly
         195                 200                 205

Gly Glu Ser Phe Gly Ile Val Val Ala Trp Gln Val Lys Leu Leu Pro
     210                 215                 220

Val Pro Pro Thr Val Thr Ile Phe Lys Ile Ser Lys Thr Val Ser Glu
225                 230                 235                 240

Gly Ala Val Asp Ile Ile Asn Lys Trp Gln Val Val Ala Pro Gln Leu
             245                 250                 255

Pro Ala Asp Leu Met Ile Arg Ile Ile Ala Gln Gly Pro Lys Ala Thr
             260                 265                 270

Phe Glu Ala Met Tyr Leu Gly Thr Cys Lys Thr Leu Thr Pro Leu Met
         275                 280                 285

Ser Ser Lys Phe Pro Glu Leu Gly Met Asn Pro Ser His Cys Asn Glu
     290                 295                 300

Met Ser Trp Ile Gln Ser Ile Pro Phe Val His Leu Gly His Arg Asp
305                 310                 315                 320

Ala Leu Glu Asp Asp Leu Leu Asn Arg Asn Asn Ser Phe Lys Pro Phe
             325                 330                 335

Ala Glu Tyr Lys Ser Asp Tyr Val Tyr Gln Pro Phe Pro Lys Thr Val
         340                 345                 350

Trp Glu Gln Ile Leu Asn Thr Trp Leu Val Lys Pro Gly Ala Gly Ile
         355                 360                 365

Met Ile Phe Asp Pro Tyr Gly Ala Thr Ile Ser Ala Thr Pro Glu Ser
         370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Ala Ala Pro Leu Ser Trp
                 405                 410                 415
```

```
Ser Lys Asp Ile Tyr Asn Tyr Met Glu Pro Tyr Val Ser Lys Asn Pro
            420                 425                 430

Arg Gln Ala Tyr Ala Asn Tyr Arg Asp Ile Asp Leu Gly Arg Asn Glu
        435                 440                 445

Val Val Asn Asp Val Ser Thr Tyr Ala Ser Gly Lys Val Trp Gly Gln
    450                 455                 460

Lys Tyr Phe Lys Gly Asn Phe Glu Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
            500

<210> SEQ ID NO 7
<211> LENGTH: 12
<212> TYPE: PRT
<213> ORGANISM: Dactylus glomerata

<400> SEQUENCE: 7

Asp Ile Tyr Asn Tyr Met Glu Pro Tyr Val Ser Lys
 1               5                  10

<210> SEQ ID NO 8
<211> LENGTH: 11
<212> TYPE: PRT
<213> ORGANISM: Dactylus glomerata

<400> SEQUENCE: 8

Val Asp Pro Thr Asp Tyr Phe Gly Asn Glu Gln
 1               5                  10

<210> SEQ ID NO 9
<211> LENGTH: 17
<212> TYPE: PRT
<213> ORGANISM: Dactylus glomerata

<400> SEQUENCE: 9

Ala Arg Thr Ala Trp Val Asp Ser Gly Ala Gln Leu Gly Glu Leu Ser
 1               5                  10                  15

Tyr

<210> SEQ ID NO 10
<211> LENGTH: 15
<212> TYPE: PRT
<213> ORGANISM: Dactylus glomerata

<400> SEQUENCE: 10

Gly Val Leu Phe Asn Ile Gln Tyr Val Asn Tyr Trp Phe Ala Pro
 1               5                  10                  15

<210> SEQ ID NO 11
<211> LENGTH: 11
<212> TYPE: PRT
<213> ORGANISM: Cynodon dactylon

<400> SEQUENCE: 11

Lys Thr Val Lys Pro Leu Tyr Ile Ile Thr Pro
 1               5                  10

<210> SEQ ID NO 12
<211> LENGTH: 22
<212> TYPE: PRT
```

```
<213> ORGANISM: Cynodon dactylon

<400> SEQUENCE: 12

Lys Gln Val Glu Arg Asp Phe Leu Thr Ser Leu Thr Lys Asp Ile Pro
 1               5                  10                  15

Gln Leu Tyr Leu Lys Ser
            20

<210> SEQ ID NO 13
<211> LENGTH: 16
<212> TYPE: PRT
<213> ORGANISM: Cynodon dactylon

<400> SEQUENCE: 13

Thr Val Lys Pro Leu Tyr Ile Ile Thr Pro Ile Thr Ala Ala Met Ile
 1               5                  10                  15

<210> SEQ ID NO 14
<211> LENGTH: 24
<212> TYPE: PRT
<213> ORGANISM: Cynodon dactylon

<400> SEQUENCE: 14

Leu Arg Lys Tyr Gly Thr Ala Ala Asp Asn Val Ile Asp Ala Lys Val
 1               5                  10                  15

Val Asp Ala Gln Gly Arg Leu Leu
            20

<210> SEQ ID NO 15
<211> LENGTH: 14
<212> TYPE: PRT
<213> ORGANISM: Cynodon dactylon

<400> SEQUENCE: 15

Lys Trp Gln Thr Val Ala Pro Ala Leu Pro Asp Pro Asn Met
 1               5                  10

<210> SEQ ID NO 16
<211> LENGTH: 15
<212> TYPE: PRT
<213> ORGANISM: Cynodon dactylon

<400> SEQUENCE: 16

Val Thr Trp Ile Glu Ser Val Pro Tyr Ile Pro Met Gly Asp Lys
 1               5                  10                  15

<210> SEQ ID NO 17
<211> LENGTH: 19
<212> TYPE: PRT
<213> ORGANISM: Cynodon dactylon
<220> FEATURE:
<221> NAME/KEY: MOD_RES
<222> LOCATION: (8)
<223> OTHER INFORMATION: variable amino acid

<400> SEQUENCE: 17

Gly Thr Val Arg Asp Leu Leu Xaa Arg Thr Ser Asn Ile Lys Ala Phe
 1               5                  10                  15

Gly Lys Tyr

<210> SEQ ID NO 18
<211> LENGTH: 23
<212> TYPE: PRT
<213> ORGANISM: Cynodon dactylon
```

<400> SEQUENCE: 18

Thr Ser Asn Ile Lys Ala Phe Gly Lys Tyr Lys Ser Asp Tyr Val Leu
1               5                   10                  15

Glu Pro Ile Pro Lys Lys Ser
            20

<210> SEQ ID NO 19
<211> LENGTH: 13
<212> TYPE: PRT
<213> ORGANISM: Cynodon dactylon

<400> SEQUENCE: 19

Tyr Arg Asp Leu Asp Leu Gly Val Asn Gln Val Val Gly
1               5                   10

<210> SEQ ID NO 20
<211> LENGTH: 15
<212> TYPE: PRT
<213> ORGANISM: Cynodon dactylon

<400> SEQUENCE: 20

Ser Ala Thr Pro Pro Thr His Arg Ser Gly Val Leu Phe Asn Ile
1               5                   10                  15

<210> SEQ ID NO 21
<211> LENGTH: 36
<212> TYPE: PRT
<213> ORGANISM: Cynodon dactylon

<400> SEQUENCE: 21

Ala Ala Ala Ala Leu Pro Thr Gln Val Thr Arg Asp Ile Tyr Ala Phe
1               5                   10                  15

Met Thr Pro Tyr Val Ser Lys Asn Pro Arg Gln Ala Tyr Val Asn Tyr
            20                  25                  30

Arg Asp Leu Asp
        35

<210> SEQ ID NO 22
<211> LENGTH: 14
<212> TYPE: PRT
<213> ORGANISM: Lolium perenne

<400> SEQUENCE: 22

Phe Leu Glu Pro Val Leu Gly Leu Ile Phe Pro Ala Gly Val
1               5                   10

<210> SEQ ID NO 23
<211> LENGTH: 9
<212> TYPE: PRT
<213> ORGANISM: Lolium perenne

<400> SEQUENCE: 23

Gly Leu Ile Glu Phe Pro Ala Gly Val
1               5

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 24
ggctcccggg gcgaaccagt ag                                              22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
accaacgcct cccacatcca gtc                                             23

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gataagcttg aattctgatt agtactttt gatcagcggc gggatgctc                  49

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gataagcttc tcgagtgatt agtactttt gatcagcggc gggatgctc                  49
```

DNA SEQUENCE, AND RECOMBINANT PREPARATION OF THE GRASS POLLEN ALLERGEN LOL P 4

BACKGROUND OF THE INVENTION

The present invention relates to the provision of a DNA sequence of the major grass pollen allergen Lol p 4. The invention also encompasses fragments, new combinations of partial sequences and point mutants having a hypoallergenic action. The recombinant DNA molecules and the derived polypeptides, fragments, new combinations of partial sequences and variants can be utilised for the therapy of pollen-allergic diseases. The proteins prepared by recombinant methods can be employed for in vitro and in vivo diagnosis of pollen allergies.

Type 1 allergies are of importance worldwide. Up to 20% of the population in industrialised countries suffer from complaints such as allergic rhinitis, conjunctivitis or bronchial asthma. These allergies are caused by allergens present in the air (aeroallergens) which are released by sources of various origin, such as plant pollen, mites, cats or dogs. Up to 40% of these type 1 allergy sufferers in turn exhibit specific IgE reactivity with grass pollen allergens (Freidhoff et al., 1986, J. Allergy Clin. Immunol. 78, 1190-2001).

The substances which trigger type 1 allergy are proteins, glycoproteins or polypeptides. After uptake via the mucous membranes, these allergens react with the IgE molecules bonded to the surface of mast cells in sensitised individuals. If two IgE molecules are crosslinked to one another by an allergen, this results in the release of mediators (for example histamine, prostaglandins) and cytokines by the effector cell and thus in the corresponding clinical symptoms.

A distinction is made between major and minor allergens, depending on the relative frequency with which the individual allergen molecules react with the IgE antibodies of allergy sufferers.

For perennial ryegrass (*Lolium perenne*), Lol p 1 has been identified as a major allergen (Freidhoff et al., 1986, J. Allergy Clin. 78:1190-1201) and its primary structure has been elucidated (Perez et al., 1990, J. Biol. Chem. 265: 16210-$16215$). A further major allergen is Lol p 2 (Freidhoff et al., 1986, J. Allergy Clin. 78:1190-1201), the primary structure of which was described in 1993 (Ansari et al., 1989, J. Biol. Chem.: 264:11181-11185). A further major allergen of perennial ryegrass is Lol p 5 (Mattiesen and Löwenstein 1991, Clin. Exp. Allergy 21: 297-307). The primary structure of Lol p 5 is also known (Ong et al., 1993, Gene 134:235-240). Perennial ryegrass furthermore contains the major allergens from groups 4 (Fahlbusch et al. 1998, Clin. Exp. Allergy 28: 799-807) and 13 (Petersen et al., 2001, J. Allergy Clin. Imm. 107:856-862).

Lol p 4 is a typical basic glycoprotein (Jaggi et al, 1989, Int. Arch. Allergy Appl. Immunol. 89:342-348, Jaggi et al., 1989, J. Allergy Clin. Immunol. 83:845-852) and is comparable with the well-studied PhI p 4, Cyn d 4 and Dac g 4 in terms of cross-reactivity with specific IgE antibodies (Haavik et al., 1985, Int. Arch. Allergy Appl. Immunol. 78:260-268; Su et al., 1991, Clin. Exp. Allergy 21:449-455; Leduc-Brodard et al., 1996, J. Allergy Clin. Immunol. 98:1065-1072; 14-17).

These homologous molecules from the *Poaceae* form allergen group 4, the molecules of which have high immunological cross-reactivity with one another both with monoclonal murine antibodies and also with human IgE antibodies (Fahlbusch et al., 1993 Clin. Exp. Allergy 23:51-60; LeducBrodard et al., 1996, J. Allergy Clin. Immunol. 98:1065-1072; Su et al., 1996, J. Allergy Clin. Immunol. 97:210; Fahlbusch et al., 1998, Clin. Exp. Allergy 28:799-807; Gavrovic-Jankulovic et al., 2000, Invest. Allergol. Clin. Immunol. 10 (6):361-367; Stumvoll et al. 2002, Biol. Chem. 383:1383-1396; Grote et al., 2002, Biol. Chem. 383:1441-1445; Andersson and Lidholm, 2003, Int. Arch. Allergy Immunol. 130:87-107; Mari, 2003, Clin. Exp. Allergy, 33 (1):43-51).

In contrast to the above-mentioned major allergens Lol p 1, Lol p 2, Lol p 5 from *Lolium perenne*, the primary structure of Lol p 4 has not yet been elucidated.

From the group 4 allergen from *Dactylus glomerate*, it has hitherto only been possible for peptides to be obtained by enzymatic degradation and sequenced:

```
                                        (SEQ ID NO 7)
DIYNYMEPYVSK, (SEQ ID NO 8)
VDPTDYFGNEQ, (SEQ ID NO 9)
ARTAWVDSGAQLGELSY
and GVLFNIQYVNYWFAP.
  (SEQ ID NO 10, Leduc-Brodard et al., 1996,
  J. Allergy Clin. Immunol. 98: 1065-1072)
```

Peptides have also been obtained from the group 4 allergen of sub-tropical Bermuda grass (*Cynodon dactylon*) by proteolysis and sequenced:

```
                                        (SEQ ID NO 11)
KTVKPLYIITP, (SEQ ID NO 12)
KQVERDFLTSLTKDIPQLYLKS, (SEQ ID NO 13)
TVKPLYIITPITAAMI, (SEQ ID NO 14)
LRKYGTAADNVIDAKVVDAQGRLL, (SEQ ID NO 15)
KWQTVAPALPDPNM, (SEQ ID NO 16)
VTWIESVPYIPMGDK, (SEQ ID NO 17)
GTVRDLLXRTSNIKAFGKY, (SEQ ID NO 18)
TSNIKAFGKYKSDYVLEPIPKKS, (SEQ ID NO 19)
YRDLDLGVNQVVG, (SEQ ID NO 20)
SATPPTHRSGVLFNI,
and AAAALPTQVTRDIYAFMTPYVSKNPRQAYVNYRDLD
  (SEQ ID NO 21, Liaw et al., 2001, Biochem.
  Biophys. Research Communication 280: 738-743).
```

For *Lolium perenne*, peptide fragments having the following sequences have been described for the basic group 4 allergen: FLEPVLGLIFPAGV (SEQ ID NO 22) and GLIEFPAGV (SEQ ID NO 23, Jaggi et al., 1989, Int. Arch. Allergy Appl. Immunol. 89: 342-348).

However, these peptide sequences which have been described for *Lolium perenne* and other group 4 allergens have hitherto not resulted in the elucidation of the primary structure of the Lol p 4 allergen.

As the first sequence of a group 4 allergen, the still unpublished sequence of Phl p 4 from *Phleum pratense* has been elucidated by the inventors of the present patent application and described in International Application WO 04/000881.

The object on which the present invention is based therefore consisted in the provision of a DNA sequence of the Lol p 4 gene encoding an allergen having the immunological properties of Lol p 4, and a corresponding recombinant DNA, on the basis of which the allergen can be expressed as protein and made available, as such or in modified form, for pharmacologically significant exploitation. The sequence of Phl p 4 was the starting point for the present invention.

LIST OF SEQUENCES ACCORDING TO THE INVENTION

DNA sequence from the Lol p 4 gene (SEQ ID NO 1).
Protein sequence derived from the DNA sequence in accordance with SEQ ID NO 1 (SEQ ID NO 2).
DNA sequence (SEQ ID NO 3), composed of nucleotides 1-200 of Phl p 4 (in accordance with SEQ ID NO 5), 201-1472 of Lol p 4 (in accordance with SEQ ID NO 1) and 1473-1503 of Phl p 4 (in accordance with SEQ ID NO 5).
Protein sequence (SEQ ID NO 4), composed of amino acids 1-67 of Phl p 4 (in accordance with SEQ ID NO 6), 68-490 of Lol p 4 (in accordance with SEQ ID NO 2) and 491-500 of Phl p 4 (in accordance with SEQ ID NO 6) having the properties, in particular immunological properties, of Lol p 4, encoded by the DNA sequence in accordance with SEQ ID NO 3.
DNA sequence of Phl p 4 (SEQ ID NO 5), in accordance with SEQ ID NO 5 from WO 04/000881.
Protein sequence of Phl p 4 (SEQ ID NO 6), in accordance with SEQ ID NO 6 from WO 04/000881.

DESCRIPTION OF THE INVENTION

The present invention provides for the first time a DNA sequence of the major grass pollen allergen Lol p 4 (SEQ ID NO 1) which encodes an allergen having the immunological properties of Lol p 4.

The present invention therefore relates to a DNA molecule encoding an allergen having the properties of Lol p 4, corresponding to a nucleotide sequence in accordance with SEQ ID NO 1.

The invention furthermore relates to a DNA molecule encoding an allergen having the properties of Lol p 4, corresponding to a nucleotide sequence in accordance with SEQ ID NO 3, composed of nucleotides 1-201 of Phl p 4 (in accordance with SEQ ID NO 5), 202-1470 of Lol p 4 (SEQ ID NO 1) and 1471-1500 of Phl p 4.

The invention furthermore relates to sequences homologous to the DNA sequences according to the invention and corresponding DNA molecules of group 4 allergens from other *Poaceae*, such as, for example, *Dactylis glomerata, Poa pratensis, Cynodon dactylon, Holcus lanatus, Secale cerale, Triticum aestivum* and *Hordeum vulgare*, which, owing to the sequence homology that exists, hybridise with the DNA sequences according to the invention under stringent conditions, or have immunological cross-reactivity with respect to Lol p 4.

The invention also encompasses fragments, new combinations of partial sequences and point mutants having a hypoallergenic action.

The invention therefore furthermore relates to corresponding partial sequences, a combination of partial sequences, or replacement, elimination or addition mutants which encode an immunomodulatory, T-cell-reactive fragment of a group 4 allergen from the *Poaceae*.

With knowledge of the DNA sequence of the naturally occurring allergens, it is now possible to prepare these allergens as recombinant proteins which can be used in the diagnosis and therapy of allergic diseases (Scheiner and Kraft, 1995, Allergy 50: 384-391).

A classical approach to effective therapeutic treatment of allergies is specific immunotherapy or hyposensitisation (Fiebig, 1995, Allergo J. 4 (6): 336-339, Bousquet et al., 1998, J. Allergy Clin. Immunol. 102 (4): 558-562). In this method, the patient is injected subcutaneously with natural allergen extracts in increasing doses. However, there is a risk in this method of allergic reactions or even anaphylactic shock. In order to minimise these risks, innovative preparations in the form of allergoids are employed. These are chemically modified allergen extracts which have significantly reduced IgE reactivity, but identical T-cell reactivity compared with the untreated extract (Fiebig, 1995, Allergo J. 4 (7): 377-382).

Even more substantial therapy optimisation would be possible with allergens prepared by recombinant methods. Defined cocktails of high-purity allergens prepared by recombinant methods, optionally matched to the individual sensitisation patterns of the patients, could replace extracts from natural allergen sources since these, in addition to the various allergens, contain a relatively large number of immunogenic, but non-allergenic secondary proteins.

Realistic perspectives which may result in reliable hyposensitisation with expression products are offered by specifically mutated recombinant allergens in which IgE epitopes are specifically deleted without impairing the T-cell epitopes which are essential for therapy (Schramm et al., 1999, J. Immunol. 162: 2406-2414).

A further possibility for therapeutic influencing of the disturbed TH cell equilibrium in allergy sufferers is immunotherapeutic DNA vaccination, which involves treatment with expressible DNA which encodes the relevant allergens. Initial experimental evidence of allergen-specific influencing of the immune response has been furnished in rodents by injection of allergen-encoding DNA (Hsu et al., 1996, Nature Medicine 2 (5): 540-544).

The present invention therefore also relates to a DNA molecule described above or below as medicament and to a corresponding recombinant expression vector as medicament.

The corresponding proteins prepared by recombinant methods can be employed for therapy and for in vitro and in vivo diagnosis of pollen allergies.

For preparation of the recombinant allergen, the cloned nucleic acid is ligated into an expression vector, and this construct is expressed in a suitable host organism. After biochemical purification, this recombinant allergen is available for detection of IgE antibodies by established methods.

The present invention therefore furthermore relates to a recombinant expression vector comprising a DNA molecule described above or below, functionally linked to an expression control sequence, and a host organism transformed with said DNA molecule or said expression vector.

The invention also relates to the use of at least one DNA molecule described above or at least one expression vector described above for the preparation of a medicament for the immunotherapeutic DNA vaccination of patients with allergies in the triggering of which group 4 allergens from the *Poaceae*, in particular Lol p 4, are involved and/or for the prevention of such allergies.

As already stated, the invention can be used as an essential component in a recombinant allergen- or nucleic acid-containing preparation for specific immunotherapy. A number of possibilities arise here. On the one hand, the protein with an unchanged primary structure may be a constituent of the preparation. On the other hand, a hypoallergenic (allergoid) form can be used in accordance with the invention for therapy in order to avoid undesired side effects by specific deletion of IgE epitopes of the molecule as a whole or the production of individual fragments which encode T-cell epitopes. Finally, the nucleic acid per se, if ligated with a eukaryotic expression vector, gives a preparation which, when applied directly, modifies the allergic immune state in the therapeutic sense.

The present invention furthermore relates to polypeptides encoded by one or more of the DNA molecules described above, preferably in their property as medicament. In particular, the polypeptides are a protein corresponding to an amino acid sequence in accordance with SEQ ID NO 2 or a protein which contains this amino acid sequence or a part of this sequence, having the properties, in particular immunological properties, of Lol p 4, and a protein corresponding to an amino acid sequence in accordance with SEQ ID NO 4 having the properties, in particular immunological properties, of Lol p 4.

Accordingly, the invention also relates to a process for the preparation of such polypeptides by cultivation of a host organism and isolation of the corresponding polypeptide from the culture.

The invention likewise relates to the use of at least one polypeptide or protein described above for the preparation of a medicament for the diagnosis and/or treatment of allergies in the triggering of which group 4 allergens from the *Poaceae*, in particular Lol p 4, are involved, and for the prevention of such allergies.

When determining the protein and DNA sequence of Lol p 4, the following procedure was followed:

The Lol p 4 DNA sequence in accordance with SEQ ID NO 1 according to the invention was amplified, cloned and sequenced by PCR with specific primers (Table 1) derived from the Phl p 4 sequence in accordance with SEQ ID NO 5 as described in WO 04/000881. A total of 7 clones were analysed. Analysis of the clones gave a uniform sequence. Three Lol p 4 DNA sequences were obtained by PCR with primers #87 and #83. The Lol p 4 DNA sequence amplified with these primers encodes the corresponding amino acids 68-401, based on the numbering of mature Phl p 4 in accordance with SEQ ID NO 6. Two further clones were obtained by PCR with primers #87 and #189. The Lol p 4 DNA sequence amplified with these primers encodes the corresponding amino acids 68-490 (numbering corresponding to Phl p 4 sequence). Two clones were obtained by PCR with primers #87 and #131. The amplified Lol p 4 DNA sequence likewise encodes the corresponding amino acids 68-490 (numbering corresponding to Phl p 4 sequence). Primers #131 and #189 correspond to the codons for the final 10 amino acids of the Phl p 4 protein and span the stop codon.

The DNA sequence in accordance with SEQ ID NO 3 according to the invention was obtained by methods known per se (PCR technique with overlapping primers).

For the preparation of the recombinant allergens according to the invention, the DNA sequences in accordance with SEQ ID NO 1 or 3 were incorporated into expression vectors (for example pProEx, pSE 380). For the N-terminal amino acids known from the protein sequencing, *E. coli*-optimised codons were used.

After transformation in *E. coli*, expression and purification of the recombinant allergens according to the invention by various separation techniques, the proteins obtained were subjected to a refolding process.

Both allergens can be employed for highly specific diagnosis of grass pollen allergies. This diagnosis can be carried out in vitro by detection of specific antibodies (IgE, IgG1-4, IgA) and reaction with IgE-loaded effector cells (for example basophiles from blood) or in vivo by skin test reactions and provocation at the reaction organ.

The reaction of the allergens according to the invention with T-lymphocytes from grass pollen allergy sufferers can be detected by allergen-specific stimulation of the T-lymphocytes for proliferation and cytokine synthesis both with T-cells in freshly prepared blood lymphocytes and also on established nLol p 4-reactive T-cell lines and clones.

The triplets encoding the cysteines were modified by site-specific mutagenesis in such a way that they encode other amino acids, preferably serine. Both variants in which individual cysteines have been replaced and those in which various combinations of 2 cysteine residues or all cysteines have been modified were prepared. The expressed proteins of these cysteine point mutants have greatly reduced or zero reactivity with IgE antibodies from allergy sufferers, but react with the T-lymphocytes from these patients.

The present invention therefore furthermore relates to a DNA molecule described above or below in which one, a plurality of or all cysteine residues of the corresponding polypeptide have been replaced by another amino acid by site-specific mutagenesis.

The immunomodulatory activity of hypoallergenic fragments which correspond to polypeptides having T-cell epitopes and that of the hypoallergenic point mutants (for example cysteine replacements) can be detected by their reaction with T-cells from grass pollen allergy sufferers.

Such hypoallergenic fragments or point mutants of the cysteines can be employed as preparations for hyposensitisation of allergy sufferers since they react with the T-cells with equal effectiveness, but result in reduced IgE-mediated side effects owing to the reduced or entirely absent IgE reactivity.

If the nucleic acids encoding the hypoallergenic allergen variants according to the invention or the unmodified DNA molecules according to the invention are ligated with a human expression vector, these constructs can likewise be used as preparations for immunotherapy (DNA vaccination).

Finally, the present invention relates to pharmaceutical compositions comprising at least one DNA molecule described above or at least one expression vector described above and optionally further active ingredients and/or adjuvants for the immunotherapeutic DNA vaccination of patients with allergies in the triggering of which group 4 allergens from the *Poaceae*, in particular Lol p 4, are involved and/or for the prevention of such allergies.

A further group of pharmaceutical compositions according to the invention comprises at least one polypeptide described above instead of the DNA and is suitable for the diagnosis and/or treatment of said allergies.

Pharmaceutical compositions in the sense of the present invention comprise, as active ingredients, a polypeptide according to the invention or an expression vector and/or respective pharmaceutically usable derivatives thereof, including mixtures thereof in all ratios. The active ingredients according to the invention can be brought into a suitable dosage form here together with at least one solid, liquid and/or semi-liquid excipient or adjuvant and optionally in combination with one or more further active ingredients.

Particularly suitable adjuvants are immunostimulatory DNA or oligonucleotides having CpG motives.

These compositions can be used as therapeutic agents or diagnostic agents in human or veterinary medicine. Suitable excipients are organic or inorganic substances which are suitable for parenteral administration and do not adversely affect the action of the active ingredient according to the invention. Suitable for parenteral use are, in particular, solutions, preferably oil-based or aqueous solutions, furthermore suspensions, emulsions or implants. The active ingredient according to the invention may also be lyophilised and the resultant lyophilisates used, for example, for the preparation of injection preparations. The compositions indicated may be sterilised and/or comprise adjuvants, such as preservatives, stabilisers and/or wetting agents, emulsifiers, salts for modifying the osmotic pressure, buffer substances and/or a plurality of further active ingredients.

Furthermore, sustained-release preparations can be obtained by corresponding formulation of the active ingredient according to the invention—for example by adsorption on aluminium hydroxide.

The invention thus also serves for improving in vitro diagnosis as part of allergen component-triggering identification of the patient-specific sensitisation spectrum. The invention likewise serves for the preparation of significantly improved preparations for the specific immunotherapy of grass pollen allergies.

TABLE 1

Primers used

| Primer number | SEQ ID NO | Sequence |
| --- | --- | --- |
| #83 | 24 | GGCTCCCGGGGCGAACCAGTAG |
| #87 | 25 | ACCAACGCCTCCCACATCCAGTC |
| #131 | 26 | GATAAGCTTGAATTCTGATTAGTAC TTTTTGATCAGCGGCGGGATGCTC |
| #189 | 27 | GATAAGCTTCTCGAGTGATTAGTAC TTTTTGATCAGCGGCGGGATGCTC |

The invention claimed is:

1. A DNA molecule encoding an Lol p 4 allergen having the amino acid sequence of SEQ ID NO: 2 or SEQ ID NO: 4, wherein the nucleotide sequence of the DNA molecule differs from SEQ ID: NO 1 and SEQ ID NO: 3, respectively, by at least once nucleotide, and wherein the nucleotide sequence has been codon optimized for the expression of said allergen polypeptide by recombinant methods in a host cell that is not a cell of *Lolium perenne*.

2. A recombinant DNA expression vector or a cloning system comprising a DNA molecule of claim 1, functionally linked to an expression control sequence.

3. A non-human host organism transformed with a DNA molecule of claim 1 or with an expression vector comprising said DNA molecule.

4. A process for the preparation of a polypeptide encoded by a DNA sequence of claim 1, comprising cultivating a host organism and isolating the corresponding polypeptide from the culture.

5. A medicament comprising a DNA molecule of claim 1.

6. A medicament comprising a recombinant expression vector of claim 2.

7. A pharmaceutical composition comprising at least one DNA molecule of claim 1 or at least one expression vector comprising said DNA molecule, and optionally comprising further active ingredients and/or adjuvants for the treatment of an allergy triggered by a group 4 allergen from *Poaceae* species by immunotherapeutic DNA vaccination of a patient having said allergy.

8. A method for the treatment of an allergy triggered by a group 4 allergen from *Poaceae* species by immunotherapeutic DNA vaccination, comprising administering to a patient in need thereof the pharmaceutical preparation of claim 7.

* * * * *